(12) United States Patent
Boser et al.

(10) Patent No.: US 8,271,100 B2
(45) Date of Patent: Sep. 18, 2012

(54) MEDICAL DEVICE CONDUCTOR JUNCTIONS

(75) Inventors: Gregory A. Boser, Richfield, MN (US); Ryan J. Collins, Minneapolis, MN (US); Mark T. Marshall, Forest Lake, MN (US); Grant H. Wurdell, Minnetonka, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 12/726,875

(22) Filed: Mar. 18, 2010

(65) Prior Publication Data

US 2010/0174350 A1 Jul. 8, 2010

Related U.S. Application Data

(63) Continuation of application No. 10/830,597, filed on Apr. 23, 2004, now Pat. No. 7,715,926.

(51) Int. Cl.
*A61N 1/05* (2006.01)
*H01R 4/24* (2006.01)
*H01R 9/053* (2006.01)

(52) U.S. Cl. ........................ 607/122; 439/909
(58) Field of Classification Search .......... 607/119–122; 439/909
See application file for complete search history.

(56) References Cited

U.S. PATENT DOCUMENTS

| | | |
|---|---|---|
| 3,953,566 A | 4/1976 | Gore |
| 4,187,390 A | 2/1980 | Gore |
| 4,573,480 A | 3/1986 | Hirschberg |
| 4,590,950 A | 5/1986 | Iwaszkiewicz et al. |
| 4,944,088 A | 7/1990 | Doan et al. |
| 5,007,435 A | 4/1991 | Doan et al. |
| 5,016,646 A | 5/1991 | Gotthardt et al. |
| 5,217,440 A | 6/1993 | Frassica |
| 5,251,643 A | 10/1993 | Osypka |
| 5,340,230 A | 8/1994 | Anderson |
| 5,358,516 A | 10/1994 | Myers et al. |
| 5,476,589 A | 12/1995 | Bacino |
| 5,483,022 A | 1/1996 | Mar |
| 5,519,172 A | 5/1996 | Spencer et al. |
| 5,522,872 A | 6/1996 | Hoff |
| 5,649,974 A | 7/1997 | Nelson et al. |
| 5,674,272 A | 10/1997 | Bush et al. |
| 5,676,694 A | 10/1997 | Boser et al. |
| 5,728,149 A | 3/1998 | Laske et al. |
| 5,796,044 A | 8/1998 | Cobian et al. |
| RE35,924 E | 10/1998 | Winkler |
| 5,845,396 A | 12/1998 | Altman et al. |
| 5,846,355 A | 12/1998 | Spencer et al. |
| 5,879,794 A | 3/1999 | Korleski, Jr. |
| 5,984,711 A | 11/1999 | Woodard |
| 6,018,683 A | 1/2000 | Verness et al. |

(Continued)

FOREIGN PATENT DOCUMENTS

EP 0 539 148 A2 4/1993

(Continued)

*Primary Examiner* — Carl H Layno
*Assistant Examiner* — Jessica Sarcione
(74) *Attorney, Agent, or Firm* — Carl F. Barry (57) ABSTRACT

A medical electrical lead includes a lead body, an inner assembly extending throught the lead body, an outer insulative layer covering the inner assembly, and an electrode mounted outside the exterior surface of the outer insulative layer. The inner assembly includes an elongate inner structure forming a lumen, an elongate conductor extending along an outer surface of the inner structure, and a conductive fitting coupled to the elongate conductor.

21 Claims, 13 Drawing Sheets

U.S. PATENT DOCUMENTS

| | | |
|---|---|---|
| 6,104,961 A | 8/2000 | Conger et al. |
| 6,159,565 A | 12/2000 | Campbell et al. |
| 6,181,971 B1 | 1/2001 | Doan |
| 6,185,463 B1 | 2/2001 | Baudino |
| 6,216,045 B1 | 4/2001 | Black et al. |
| 6,249,708 B1 | 6/2001 | Nelson et al. |
| 6,259,954 B1 | 7/2001 | Conger et al. |
| 6,266,563 B1 | 7/2001 | KenKnight et al. |
| 6,366,819 B1 | 4/2002 | Stokes |
| 6,366,820 B1 | 4/2002 | Doan et al. |
| 6,451,396 B1 | 9/2002 | Zumbrum et al. |
| 6,493,590 B1 | 12/2002 | Wessman et al. |
| 6,501,991 B1 | 12/2002 | Honeck et al. |
| 6,505,401 B1 | 1/2003 | Doan |
| 6,647,291 B1 | 11/2003 | Bonner et al. |
| 6,673,455 B2 | 1/2004 | Zumbrum et al. |
| 7,039,470 B1 | 5/2006 | Wessman |
| 7,239,922 B1 | 7/2007 | Boogaard et al. |
| 7,715,926 B2 * | 5/2010 | Boser et al. .................. 607/122 |
| 2001/0023368 A1 | 9/2001 | Black et al. |
| 2002/0038139 A1 | 3/2002 | Wessman et al. |
| 2002/0143377 A1 | 10/2002 | Wessman et al. |
| 2002/0183822 A1 | 12/2002 | Bodner |
| 2003/0139794 A1 | 7/2003 | Jenney et al. |
| 2005/0113898 A1 | 5/2005 | Honeck et al. |
| 2005/0240252 A1 | 10/2005 | Boser et al. |
| 2006/0265037 A1 | 11/2006 | Kuzma et al. |
| 2007/0106144 A1 | 5/2007 | Squeri et al. |
| 2007/0276458 A1 | 11/2007 | Boser |
| 2009/0125089 A1 | 5/2009 | Bischoff et al. |
| 2009/0192576 A1 | 7/2009 | Seifert et al. |
| 2009/0254162 A1 | 10/2009 | Quinci et al. |

FOREIGN PATENT DOCUMENTS

| | | |
|---|---|---|
| EP | 0 539 148 A3 | 9/1993 |
| WO | WO 94/13358 A1 | 6/1994 |
| WO | WO 02/089909 A1 | 11/2002 |

* cited by examiner

MEDICAL DEVICE CONDUCTOR JUNCTIONS

This is a continuation of U.S. patent application Ser. No. 10/830,597, filed Apr. 23, 2004, and issued as U.S. Pat. No. 7,715,926, which is incorporated herein by reference.

TECHNICAL FIELD

The present invention relates to elongated medical devices and more particularly to novel conductor junctions.

BACKGROUND

Cardiac stimulation systems commonly include a pulse-generating device, such as a pacemaker or implantable cardioverter/defibrillator that is electrically connected to the heart by at least one electrical lead. An electrical lead delivers electrical pulses from the pulse generator to the heart, stimulating the myocardial tissue via electrodes included on the lead. Furthermore, cardiac signals may be sensed by lead electrodes and conducted, via the lead, back to the device, which also monitors the electrical activity of the heart.

Medical electrical leads are typically constructed to have the lowest possible profile without compromising functional integrity, reliability and durability. Often junctions formed between a conductor and other components included in leads, for example electrodes, can increase the lead's profile, therefore it is desirable to develop low profile junctions.

BRIEF DESCRIPTION OF THE DRAWINGS

The following drawings are illustrative of particular embodiments of the invention and therefore do not limit its scope, but are presented to assist in providing a proper understanding of the invention. The drawings are not to scale (unless so stated) and are intended for use in conjunction with the explanations in the following detailed description. The present invention will hereinafter be described in conjunction with the appended drawings, wherein like numerals denote like elements, and.

DETAILED DESCRIPTION

The following detailed description is exemplary in nature and is not intended to limit the scope, applicability, or configuration of the invention in any way. Rather, the following description provides a practical illustration for implementing exemplary embodiments of the invention.

Figure 1:
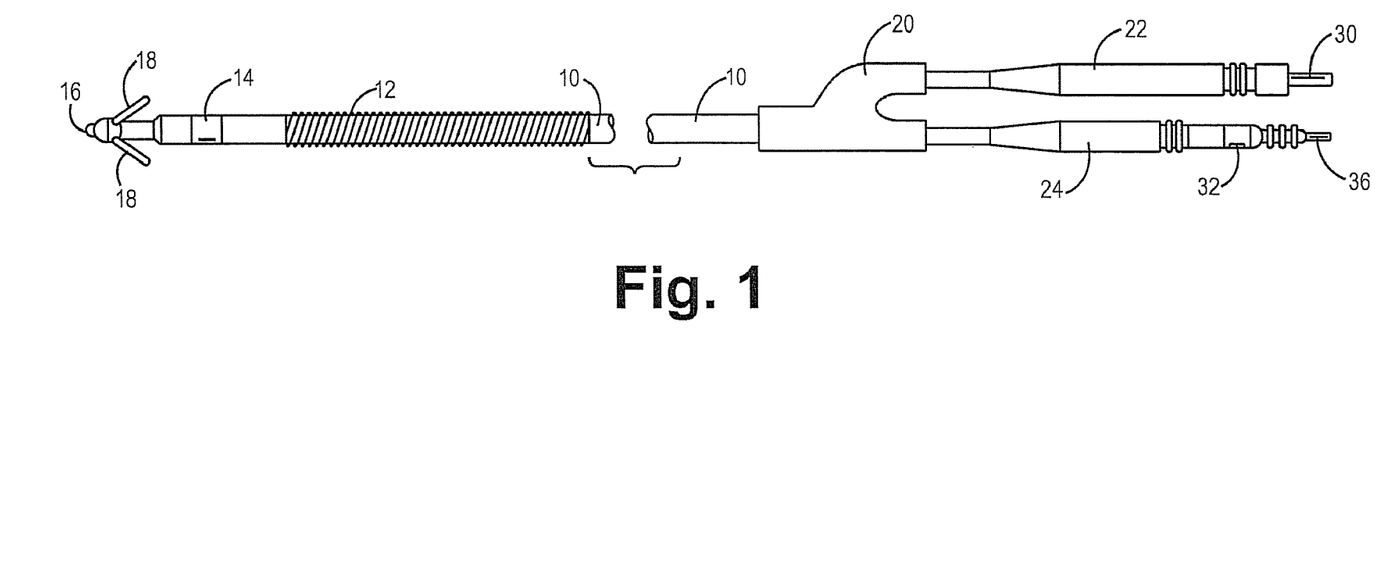
FIG. 1 is a plan view of an exemplary medical electrical lead in which embodiments of the present invention may be incorporated.

FIG. 1 is a plan view of an exemplary medical electrical lead in which embodiments of the present invention may be incorporated. FIG. 1 illustrates a lead including a lead body 10 extending distally from a transition sleeve 20 to a distal end, which includes an electrode tip 16, tines 18 and an electrode ring 14; a defibrillation coil 12 extends along a portion of lead body 10 in proximity to the distal end. FIG. 1 further illustrates connector legs 22 and 24, which are adapted to couple lead to a medical device according to means well known to those skilled in the art, extending proximally from transition sleeve 20; conductors (not shown) extending through lead body 10, transition sleeve 20 and legs 24, 22 couple electrodes 16, 14 and 12 to connector contacts 36, 32 and 30, respectively, of connector legs 24 and 22. Embodiments of the present invention include means for coupling electrodes mounted about a lead body, for example defibrillation coil 12 or electrode ring 14, to a conductive wire or cable extending within the lead body.

Figure 2A:
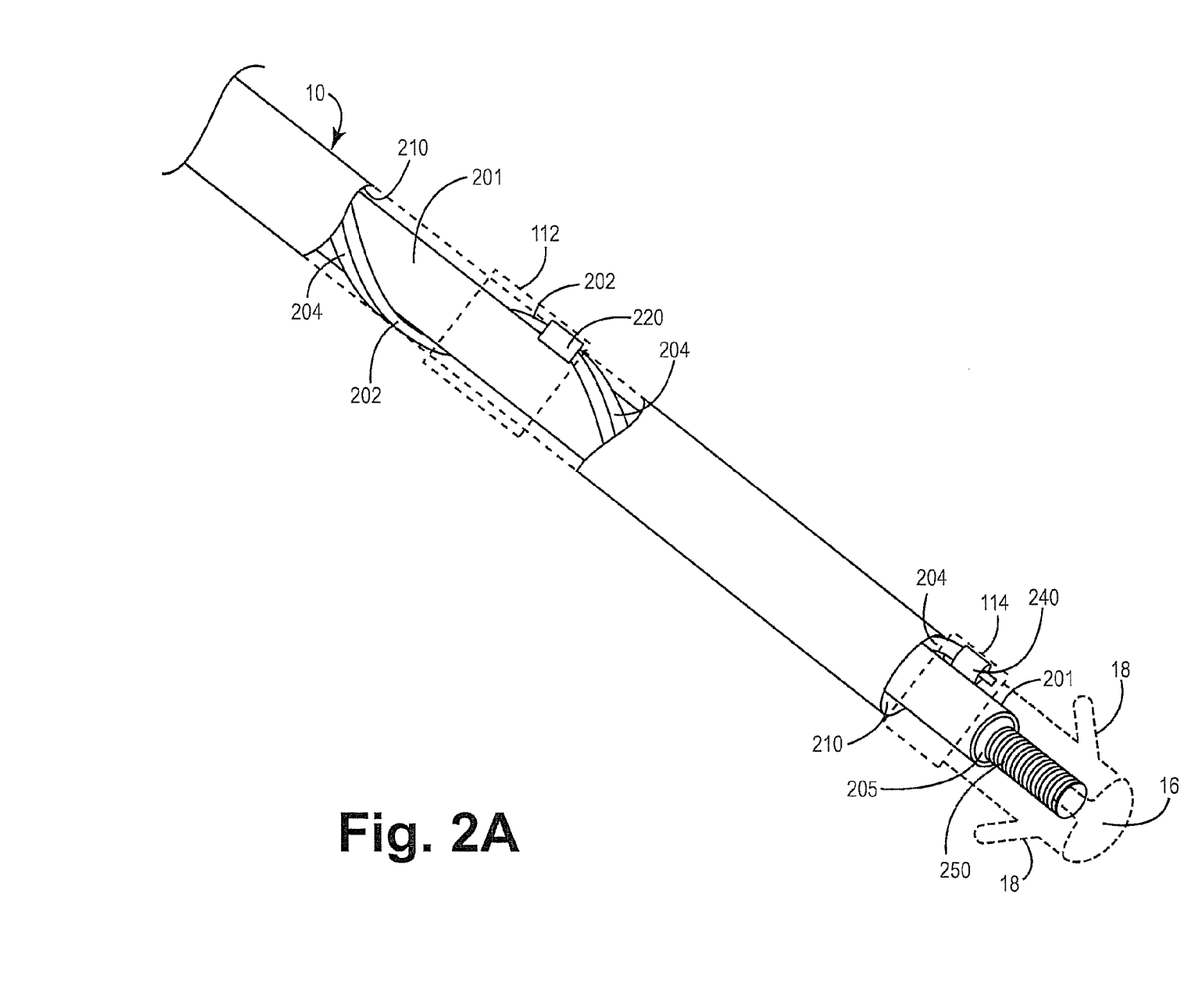
FIGS. 2A-B are perspective views of portions of the exemplary lead according to embodiments of the present invention.
Figure 2B:
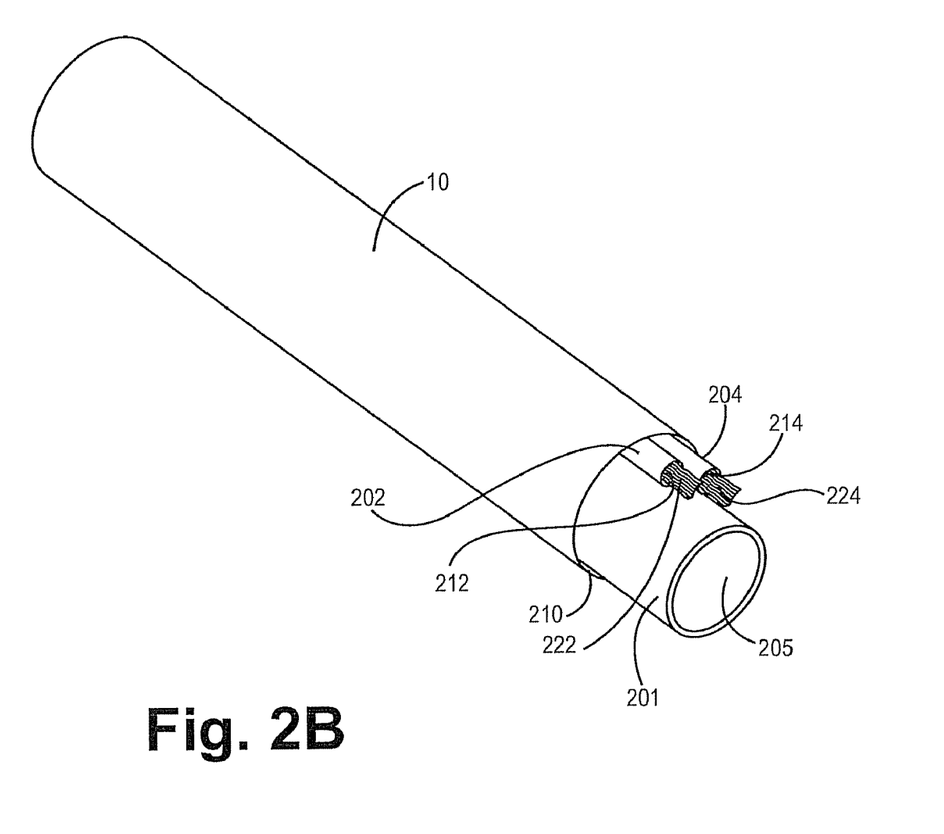

FIGS. 2A-B are perspective views of portions of the exemplary lead according to embodiments of the present invention. Via cut-away views, FIG. 2A illustrates lead body 10 including an inner elongate structure 201 about which a first conductor 202 and a second conductor 204 are positioned; a first conductive fitting 220 and a second conductive fitting 240 are coupled to first and second conductors 202 and 204, respectively. According to the illustrated embodiment, elongate structure 201 includes a lumen 205 in which an inner conductor 250 extends. According to an exemplary embodiment of the present invention lumen 205 has a diameter between approximately 0.01 and 0.03 inches. Using dashed lines, FIG. 2A further illustrates the extension of an outer insulative layer 210 over the subassembly, a first electrode 112 and a second electrode 114 coupled to conductors 202 and 204 via fittings 220 and 240, respectively, and a distal end of lead body 10 terminated by electrode tip 16, which is coupled to inner conductor 250, and tines 18. According to embodiments of the present invention at least first conductive fitting 220 is coupled to conductor 202, before covering the subassembly (formed, as illustrated, of inner elongate structure 201, conductors 202, 204 and fitting 202) with outer insulative layer 210. FIG. 2B illustrates a portion of lead body 10, according to one embodiment, before electrodes are coupled.

FIG. 2B further illustrates conductors 202, 204 each comprising a cable 222, 224, formed of a plurality of conductive wires bundled together, and an outer insulative layer 212, 214. According to alternate embodiments, conductors are each formed of a single wire; furthermore, although conductors 202 and 204 are shown wrapped or wound about inner elongate structure 201 in FIG. 2A, conductors 202 and 204 according to alternate embodiments can be positioned approximately linearly along inner elongate structure 201. An example of an appropriate material for conductor wires employed by embodiments of the present invention is an MP35N alloy; one or more conductor wires may further include a low resistance core, for example silver. An example of an appropriate material for insulative layers 212, 214 is ETFE, which may be formed as a jacket extruded about cables 222, 224 prior to positioning conductors 202, 204 along structure 201. According to some embodiments of the present invention, elongate structure 201 is formed from an insulative material, examples of which include fluoropolymers, silicones, and polyurethanes. It should be noted that when conductors 202, 204 are positioned along structure 201 they can be embedded in an outer surface of structure 201 according to some embodiments.

Figure 3A:
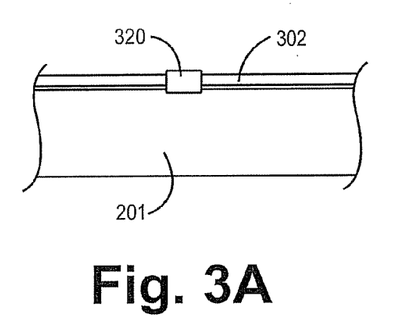
FIGS. 3A-B are plan views, each of a portion of a lead subassembly according to alternate embodiments of the present invention.
Figure 3B:
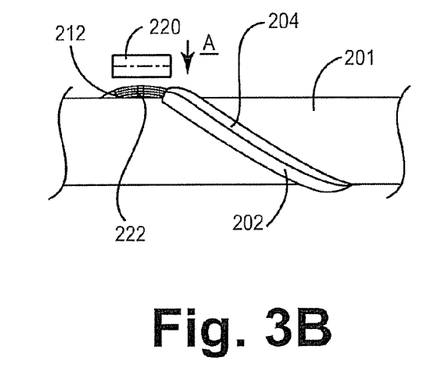

FIGS. 3A-B are plan views, each of a portion of a lead subassembly according to alternate embodiments of the present invention. FIG. 3A illustrates a subassembly of elongate structure 201 on which a conductor 302 including a conductive fitting 320 coupled thereto is positioned; according to this embodiment, conductive fitting 320 is coupled to conductor 302 prior to positioning conductor on elongate structure 201. FIG. 3B illustrates conductive fitting 220 being directed, per arrow A, toward a portion of conductor 202 where insulative layer 212 has been removed to expose cable 222 in order to couple fitting 220 to conductor 202; according to this alternate embodiment, fitting 220 is coupled to conductor 202 after conductors 202 and 204 have been positioned on structure 201. It should be noted that although FIG. 3B shows insulative layer 212 removed for coupling with fitting 220, other types of fittings having internal features to penetrate layer 212 may be employed so that layer 212 need not be removed for coupling. Furthermore, according to other embodiments of the present invention a fitting is coupled to a conductor, for example fitting 220 of conductor 202 (FIG. 2A), before an outer insulative layer, for example outer insulative layer 212 about cable 222 (FIG. 2B), is formed. According to these embodiments, the conductor and fitting are covered with an outer insulative layer, which is subsequently removed in proximity to the fitting, either before positioning the conductor including the fitting on elongate structure 201 or afterwards, and may be in conjunction with providing an opening in outer insulative layer 210. Means for removing the insulation in proximity to the fitting are well known to those skilled in the art and include but are not limited to, mechanical and laser stripping.

Figure 4A:
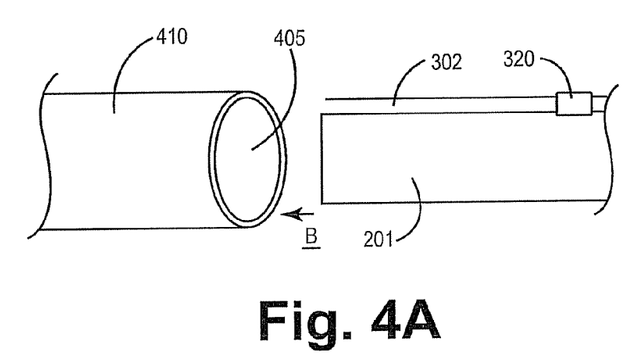
FIGS. 4A-C are schematics, each showing a step of an assembly method according to alternate embodiments of the present invention.
Figure 4B:
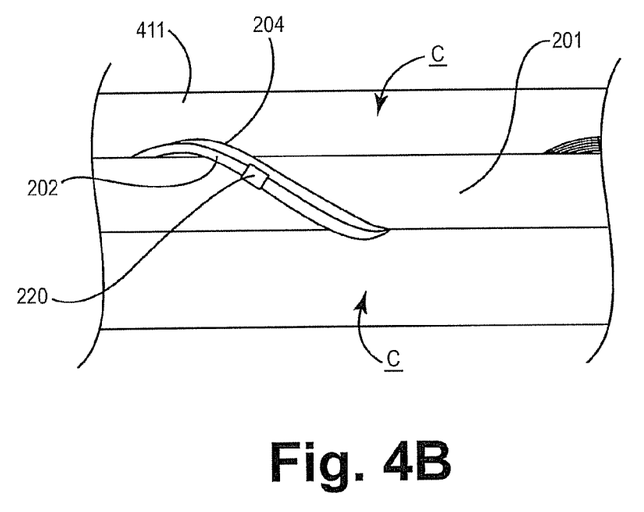

FIGS. 4A-C are schematics, each showing a step of an assembly method according to alternate embodiments of the present invention. FIG. 4A illustrates the subassembly shown in FIG. 3A directed, per arrow B, toward a lumen 405 of an outer insulative layer 410; according to this embodiment of the present invention, outer insulative layer 410 is formed as a generally tubular structure and the subassembly is inserted therein. FIG. 4B illustrates the subassembly shown in FIG. 3B, after fitting 220 is coupled to conductor 202, positioned in proximity to an outer insulative layer 411; according this other embodiment, outer insulative layer 411 is initially formed as a sheet and is wrapped about the subassembly per arrows C and then bonded along a seam formed when opposing edges of layer 411 come together. Suitable materials for layers 410, 411 include, but are not limited to, silicones, polyurethanes and fluoropolymers.

Figure 4C:
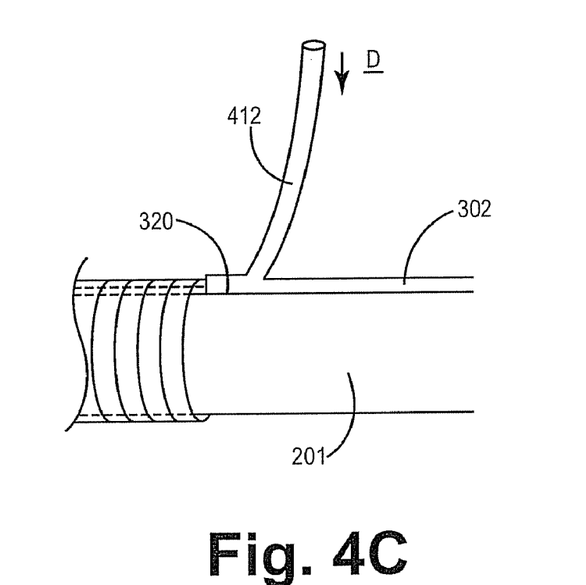

FIG. 4C illustrates the subassembly shown in FIG. 3A about which an outer insulative layer 412 is being wrapped per arrow D. According to yet another embodiment of the present invention, outer insulative layer 412 is in the form of a tape which is wrapped about the subassembly to form a lead body, the longitudinal edges of the tape being bonded or sintered together during or following the wrapping process. An example of a wrapping process is described in International Publication Number WO 02/089909 in conjunction with FIGS. 4 and 5; FIGS. 4 and 5 of WO 02/089909 along with associated descriptions therein are incorporated by reference herein. Although WO 02/089909 describes the process for covering a defibrillation electrode with e-PTFE, the inventors contemplate using the process in conjunction with an insulative fluoropolymer material to form outer insulative layer 412 according to some embodiments of the present invention.

Figure 4D:
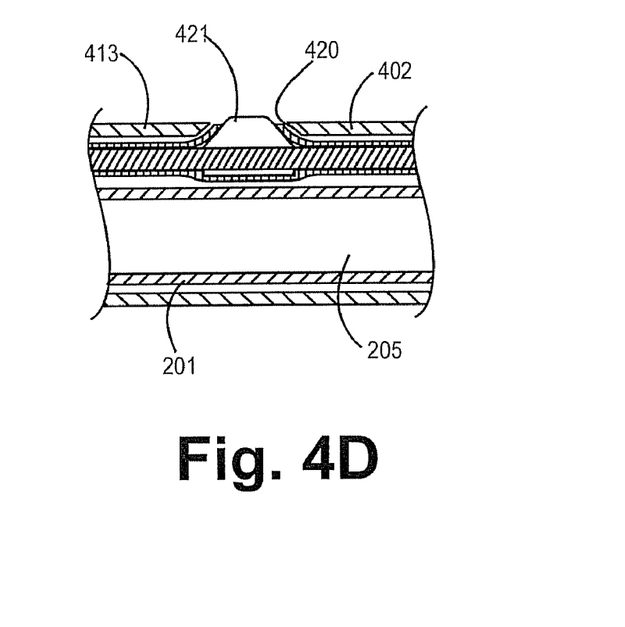
FIG. 4D is a section view of a lead assembly according to one embodiment of the present invention.

FIG. 4D is a section view of a lead assembly according to an embodiment of the present invention. FIG. 4D illustrates a conductor 402 and a conductive fitting 421 coupled thereto positioned along elongate structure 201, and an insulative layer 413 including an opening through which a protrusion 421 of conductive fitting 420 extends. According to one method of the present invention, layer 413 is applied as a coating, either by an extrusion or a dip process, and the opening is formed during the coating process by means of protrusion 421 of fitting 420 penetrating through the applied coating. Referring back to FIG. 4C, an alternate method for forming an opening for fitting 320 is to leave an opening or a gap in the wrap of insulative layer 412. Suitable materials for layer 413 include, but are not limited to, silicones, polyurethanes and fluoropolymers.

Figure 5A:
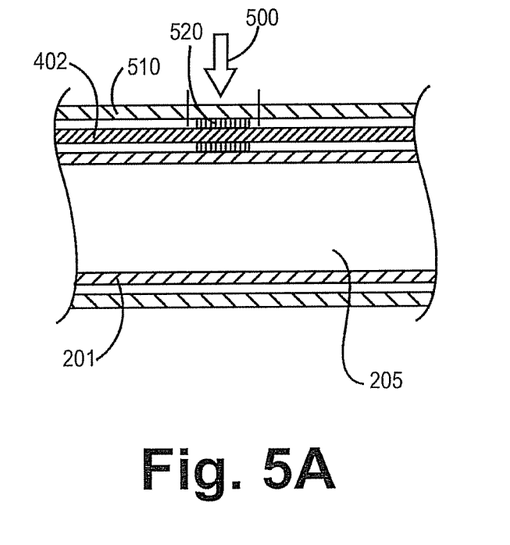
FIGS. 5A-B are section views showing steps of assembly methods according to alternate embodiments of the present invention.
Figure 5B:
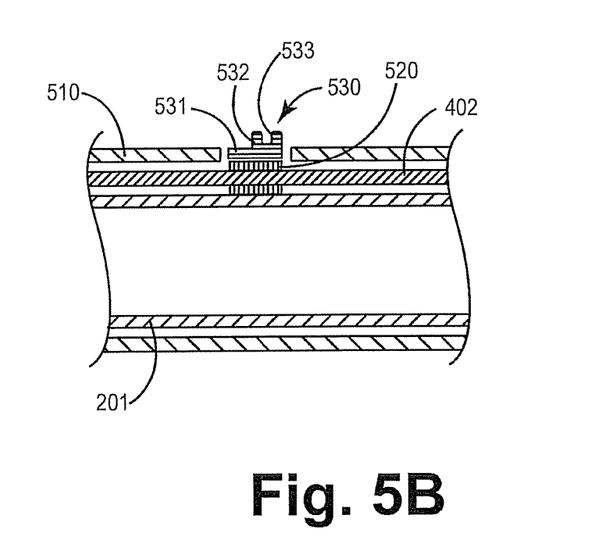

FIGS. 5A-B are section views showing steps of assembly methods according to alternate embodiments of the present invention. FIG. 5A illustrates a conductor 402 and a conductive fitting 520 coupled thereto positioned along elongate structure 201 and an insulative layer 510 formed thereover wherein a step to form an opening in proximity to fitting 520 is shown as arrow 500. According to one embodiment the opening is formed by mechanical cutting; according to another embodiment the opening is formed by ablation, i.e., laser; according to yet another embodiment an application of heat energy causing material flow forms the opening either independently or in conjunction with mechanical cutting. Means for forming the opening according to these embodiments are well known to those skilled in the art. FIG. 5B illustrates a subsequent step in an assembly method wherein, following the formation of the opening, fitting 520 is augmented with an attachment 530, which includes a protrusion 532 extending out through the opening to facilitate electrode coupling. According to the illustrated embodiment, attachment 530 further includes a portion 531 adapted for coupling with fitting 520, for example by welding, and a groove 533 adapted for coupling with an electrode, for example a filar of coil electrode 12 shown in FIG. 1. According to alternate embodiments, fitting 520 need not be augmented and an electrode includes an inwardly projecting feature to couple with fitting within or below opening; such embodiments are described in greater detail in conjunction with FIGS. 6 and 7D.

Figure 6:
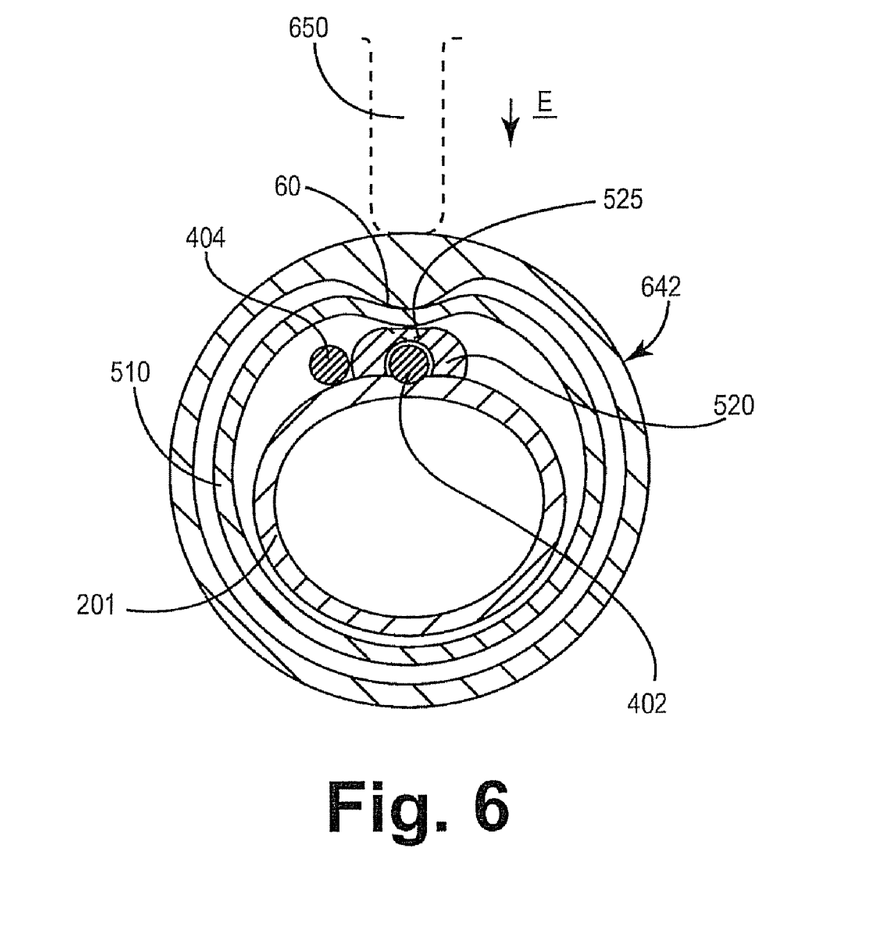
FIG. 6 is a section view showing a step of an assembly method according to an alternate embodiment of the present invention.

FIG. 6 is a section view showing a step of an assembly method according to an alternate embodiment of the present invention wherein forming an opening in proximity to a fitting is accomplished when an electrode is coupled to the fitting. FIG. 6 illustrates an electrode 642 mounted about a lead body formed by inner elongate structure 201, conductors 402, 404 positioned along the structure 201, conductive fitting 520 coupled to conductor 402 and insulative layer 510 formed thereover. FIG. 6 further illustrates electrode 642 including an internal feature 60 which is adapted to penetrate through layer 510 as a tooling head 650 is pressed against electrode 642 per arrow E; according to one embodiment, tooling head 650 is used for staking electrode 624 to fitting 520 and feature 60 penetrates by means of mechanical cutting; according to another embodiment tooling head 650 is used for resistance welding electrode 624 to fitting 520 by means of a current passed through head 650 and conductor 402 such that penetration is made via thermally assisted flow of material forming layer 510. Dashed lines in FIG. 6 illustrate a groove 525 which may be faulted in fitting 520 and dimensioned to receive feature 60 of electrode as it is pressed inward; according to one embodiment groove 525 serves to facilitate the penetration of feature 60 through layer 510 which would be spread taut across groove during a previous assembly step.

Figure 7A:
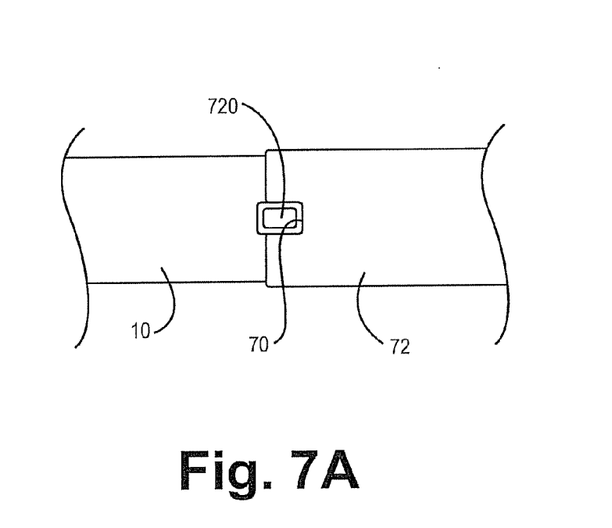
FIG. 7A is a plan view of a portion of a lead according to one embodiment of the present invention.
Figure 7B:
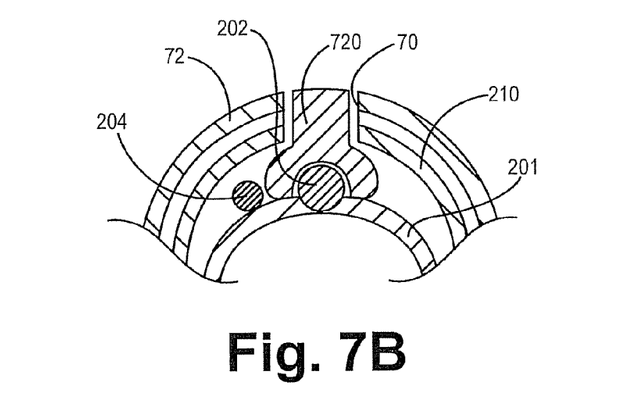
FIG. 7B is a section view of a segment of the portion of the lead shown in FIG. 7A.
Figure 7C:
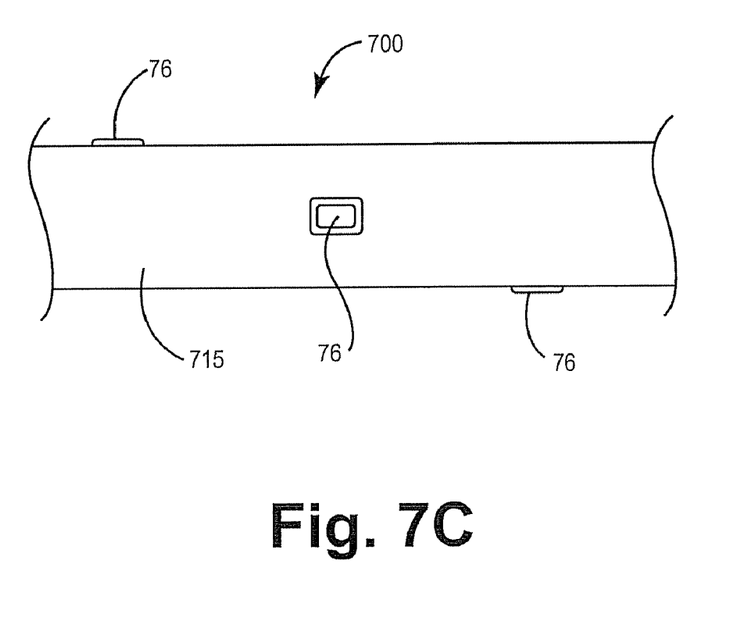
FIG. 7C is a plan view of a lead according to another embodiment of the present invention.

FIG. 7A is a plan view of a portion of a lead according to one embodiment of the present invention and FIG. 7B is a section view of a segment of the portion of the lead shown in FIG. 7A. FIG. 7A illustrates electrode 72 mounted on lead body 10 and including a feature formed as a slot 70 into which a protruding portion of a fitting 720 is inserted for coupling, for example by laser welding. The section view of FIG. 7B further illustrates fitting 720 coupled to conductor 202 and the protruding portion of fitting 720 extending through an opening in outer insulative layer 210 to fit within slot 70 of electrode 72. FIG. 7C is a plan view of a lead according to another embodiment of the present invention wherein a protruding portion of fitting 720 includes an electrode surface 76 formed directly thereon, eliminating the need for an additional electrode component; as illustrated in FIG. 7C a plurality of fittings 720 may be positioned along a lead body 715 to provide multiple electrode surfaces 75.

Figure 7D:
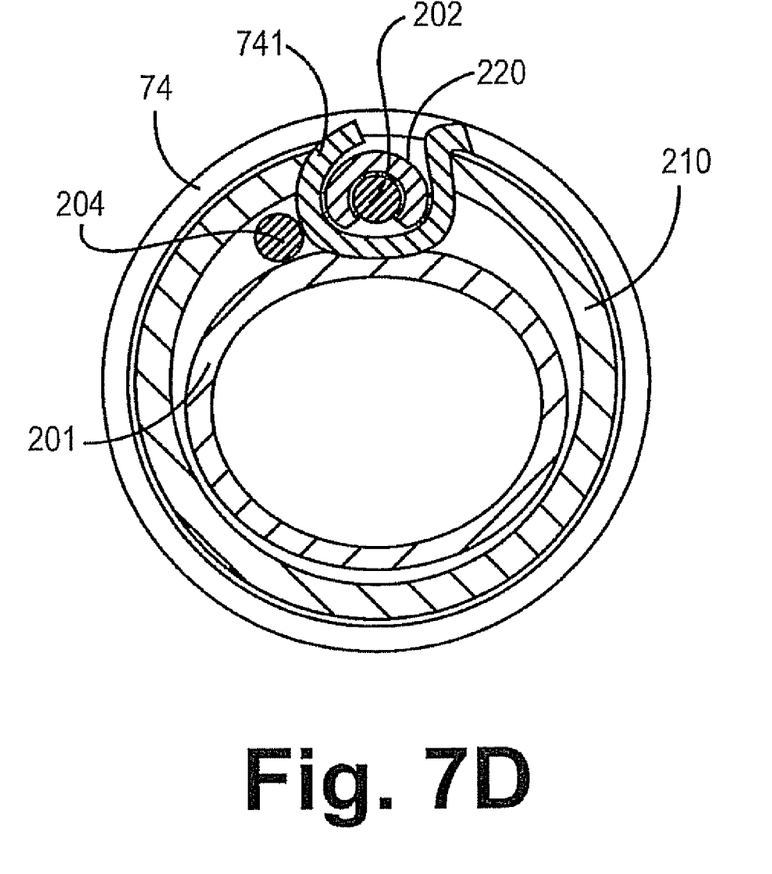
FIG. 7D is a section view of a lead according to yet another embodiment of the present invention.

FIG. 7D is a section view of a lead according to another embodiment of the present invention wherein a conductive fitting is inserted into an electrode feature for coupling. FIG. 7D illustrates an electrode 74 mounted on lead body 10 and including a hook-like feature 741 extending inward through the opening in outer insulative layer 210 to engage and couple with fitting 220, which is coupled to conductor 202. Hook-like feature 741 may be coupled to fitting 220 by means of crimping or laser welding.

Figure 8A:
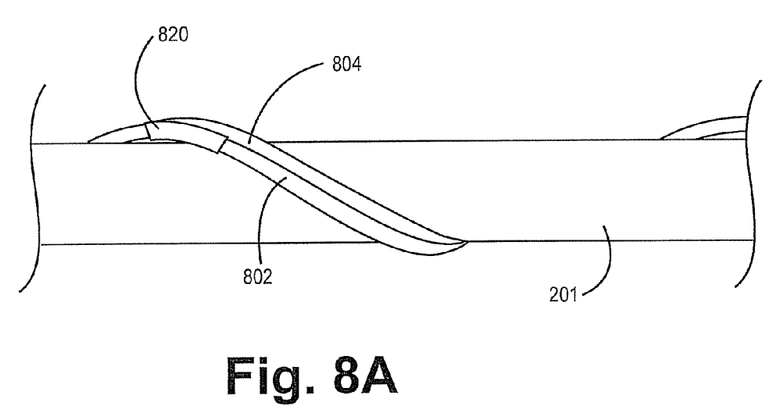
FIG. 8A is a plan view of a lead subassembly according to one embodiment of the present invention.
Figure 8B:
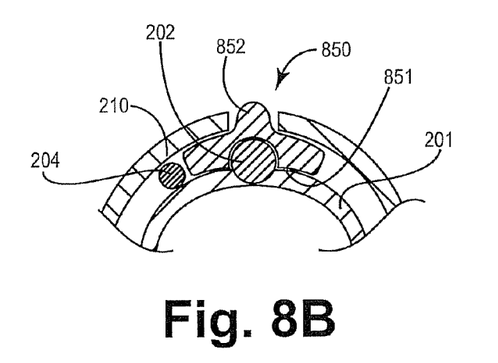
FIG. 8B is a section view of a lead assembly according to another embodiment of the present invention.

FIG. 8A is a plan view of a lead subassembly according to one embodiment of the present invention and FIG. 8B is a section view of a lead subassembly according to another embodiment of the present invention wherein fittings include surfaces conforming to a contour of the subassemblies. FIG. 8A illustrates the subassembly including inner elongate structure 201, a first conductor 802, a second conductor 804 and a flexible fitting 820 coupled to first conductor 802. Flexible fitting 820 may be formed of a conductive polymer, examples of which include intrinsically conductive polymers, such as polyacetylene and polypyrrole, and conductor-filled polymers, such as silicone rubber having embedded metallic, carbon, or graphite particles; once formed fitting 820 may be assembled about conductor 802 into a close fitting relationship, i.e. an interference fit, or fitting 820 may be formed in situ about conductor 802, for example by a molding process. Examples of metallic conductors, which may be used for any of the fitting embodiments described herein include, but are not limited to, platinum, platinum-iridium alloys, stainless steel and titanium.

FIG. 8B illustrates the subassembly including inner elongate structure 201, first conductor 202, second conductor 204 and a fitting 850 coupled to conductor 202; fitting 850 includes a surface 851 conforming to a contour of structure 201 and a protrusion 852 extending from an opposite side of surface 851 out through the opening in layer 210. According to the embodiments illustrated in FIGS. 8A-B positioning of conductors 802 and 202 about structure 201, after the fittings are coupled to the conductors, may be facilitated by the conforming fittings.

Figure 9:
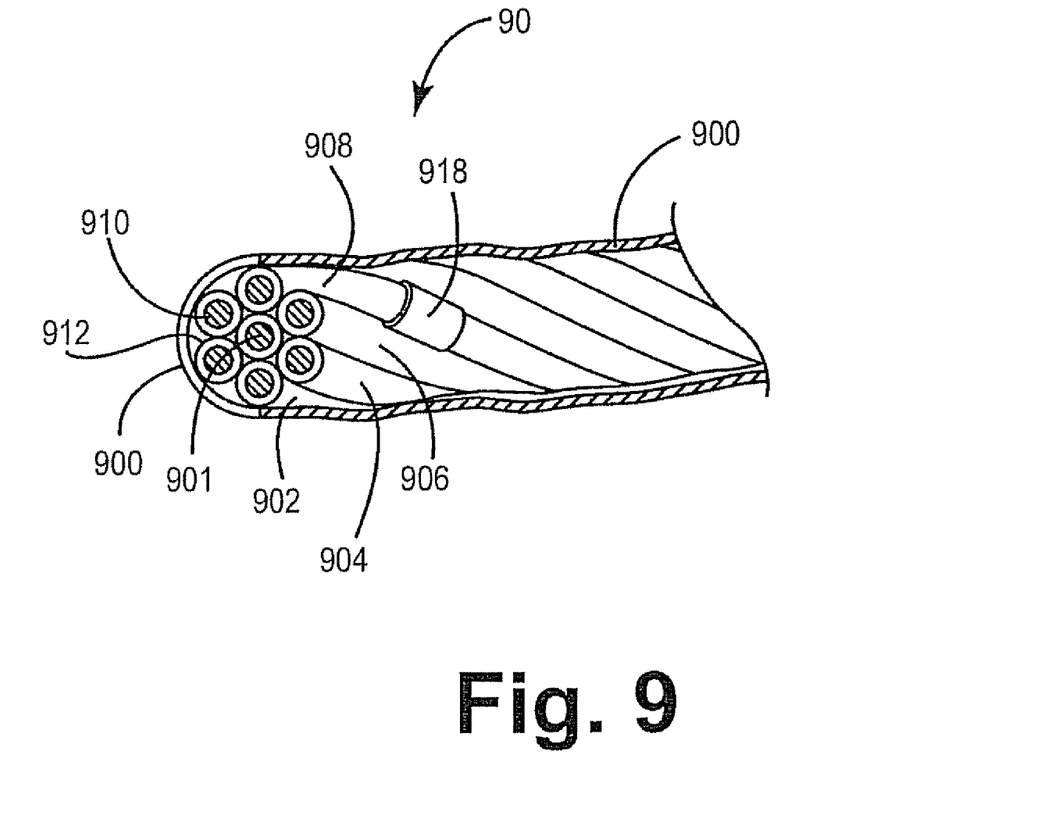
FIG. 9 is a perspective view of an alternate embodiment of a portion of a lead subassembly.

FIG. 9 is a perspective view of an alternate embodiment of a portion of a lead subassembly including a cut-away cross-section and a partial longitudinal cut-away section. FIG. 9 illustrates a lead body 90 including an insulative layer 900 covering an elongate structure 901 formed by an insulated conductor about which additional insulated conductors 902, 904, 906, 908, 910 and 912 are wrapped; a conductive fitting 918 has been coupled to conductor 908 prior to covering the subassembly with insulative layer 900. As previously described for other embodiments of the present invention, conductive fitting 918 may be coupled to conductor 908 either before or after positioning conductor along elongate structure 901; an opening subsequently formed in layer 900, either during or after the covering process, will expose fitting 918 for electrode coupling.

In each of the above described embodiments the openings through which couplings are made between electrodes and conductor fittings may be sealed with an adhesive, for example silicone medical adhesive or polyurethane adhesive, to prevent fluid ingress; sealing may be performed either before or after the coupling depending upon the embodiment.

Finally, it will be appreciated by those skilled in the art that while the invention has been described above in connection with particular embodiments and examples, the invention is not necessarily so limited; numerous other embodiments and uses are intended to be encompassed by the claims attached hereto. For example a host of other types of medical devices including electrical mapping catheters, ablation catheters and neurological stimulation devices may employ embodiments of the present invention.

What is claimed is:

1. A medical electrical lead, comprising:
    an inner assembly comprising:
        an elongate inner structure,
        an elongate conductor subassembly positioned about and extending along an outer surface of the elongate inner structure, wherein the elongate conductor subassembly comprises:
            an elongate conductor, and
            a conductive fitting, wherein the conductive fitting is assembled about and coupled to at least a portion of the elongate conductor, wherein the conductive fitting comprises an inner surface formed at least partially about the elongate conductor and an outer surface opposite the inner surface;
    an outer insulative layer covering the inner assembly and in contact with at least a portion of the outer surface of the conductive fitting, the outer insulative layer including an opening in proximity to the conductive fitting, wherein the conductive fitting is coupled to the elongate conductor prior to the inner assembly being covered by the outer insulative layer; and
    an electrode mounted about the outer insulative layer and coupled via the opening to a portion of the conductive fitting opposite the inner surface formed at least partially about the elongate conductor;
    wherein the conductive fitting conforms to a contour of the inner assembly.

2. The lead of claim 1, wherein at least a portion of the inner surface conforms to at least a portion of the outer surface of the elongate inner structure.

3. The lead of claim 1, wherein the conductive fitting is flexible.

4. The lead of claim 1, wherein the conductive fitting further includes a feature protruding outward through the opening for the coupling with the electrode.

5. The lead of claim 1, wherein the elongate inner structure includes a lumen extending therethrough along a length of the structure.

6. The lead of claim 5, further comprising a second elongate conductor extending within the lumen.

7. The lead of claim 5, wherein the lumen is approximately coaxial with the outer surface of the elongate inner structure.

8. The lead of claim 6, further comprising a distal tip electrode coupled to the second elongate conductor.

9. The lead of claim 1, further comprising:
 a second electrode mounted about the outer insulative layer; and
 wherein the inner assembly further comprises a second elongate conductor subassembly, wherein the second elongate conductor subassembly comprises a second elongate conductor extending along the outer surface of the elongate inner structure and a second conductive fitting assembled about and coupled to at least a portion of the second elongate conductor;
 the outer insulative layer further includes a second opening in proximity to the second conductive fitting;
 wherein the second electrode is coupled to the second conductive fitting via the second opening.

10. The lead of claim 9, wherein the elongate inner structure includes a lumen extending therethrough along a length of the structure.

11. The lead of claim 10, further comprising a third elongate conductor extending within the lumen.

12. The lead of claim 11, further comprising a distal tip electrode coupled to the third elongate conductor.

13. The lead of claim 10, wherein the lumen is approximately coaxial with the outer surface of the elongate inner structure.

14. A medical electrical lead, comprising:
 an elongate inner structure;
 an elongate conductor having a conductive fitting assembled about and coupled to at least a portion of the elongate conductor prior to the elongate conductor being positioned about an outer surface of the elongate inner structure, wherein the conductive fitting comprises an inner surface adjacent the elongate conductor and an outer surface opposite the inner surface;
 an outer insulative layer covering the elongate inner structure and in contact with at least a portion of the outer surface of the conductive fitting, wherein an opening is defined in the outer insulative layer in proximity to the conductive fitting; and
 an electrode mounted about the outer insulative layer and coupled via the opening to a portion of the conductive fitting opposite the inner surface thereof, wherein at least a portion of the conductive fitting conforms to a contour of the outer surface of the elongate inner structure.

15. The lead of claim 14, wherein the conductive fitting is flexible.

16. The lead of claim 14, wherein the conductive fitting further includes a feature protruding outward through the opening opposite the inner surface of the conductive fitting for coupling with the electrode.

17. The lead of claim 14, further comprising:
 a second elongate conductor having a second conductive fitting assembled about and coupled to at least a portion of the second elongate conductor prior to the second elongate conductor being positioned about the outer surface of the elongate inner structure, wherein the second conductive fitting comprises an inner surface adjacent the elongate conductor, wherein the outer insulative layer covers the elongate inner structure having the elongate conductor and the second elongate conductor positioned about the outer surface thereof, wherein a second opening is defined in the outer insulative layer in proximity to the second conductive fitting; and
 a second electrode mounted about the outer insulative layer and coupled via the second opening to a portion of the second conductive fitting opposite the inner surface thereof, wherein at least a portion of the second conductive fitting conforms to a contour of the outer surface of the elongate inner structure.

18. The lead of claim 17, wherein the elongate inner structure includes a lumen extending therethrough along a length of the structure.

19. The lead of claim 18, further comprising a third elongate conductor extending within the lumen.

20. The lead of claim 19, further comprising a distal tip electrode coupled to the third elongate conductor.

21. The lead of claim 18, wherein the lumen is approximately coaxial with the outer surface of the elongate inner structure.

* * * * *